United States Patent [19]

Krumeich

[11] Patent Number: 4,695,458
[45] Date of Patent: Sep. 22, 1987

[54] SOLUTION OF ALPHA-CHYMOTRYPSIN

[76] Inventor: Jorg H. Krumeich, Probst-Hellmich-Promenade 28, 4630 Bochum 6, Fed. Rep. of Germany

[21] Appl. No.: 826,337

[22] Filed: Feb. 5, 1986

[51] Int. Cl.$^4$ .............................................. A61K 37/48
[52] U.S. Cl. ....................................... 424/94; 514/912
[58] Field of Search ........................... 424/94; 514/912

[56] References Cited

U.S. PATENT DOCUMENTS 3,860,702  1/1975  Buell ...................................... 424/94
4,514,388  4/1985  Psaledakis .............................. 424/94
4,520,019  5/1985  Ribi et al. .......................... 424/195.1

Primary Examiner—Johnnie R. Brown
Assistant Examiner—John W. Rollins, Jr.
Attorney, Agent, or Firm—Thomas H. Murray; Clifford A. Poff

[57] ABSTRACT

Use of a solution of alpha-chymotrypsin in a physiological solution medium, especially of a physiological saline solution or of a solution of glutathion-bicarbonate according to Edelhauser in a dilution of 1:20,000 to 1:30,000, preferably 1:25,000, corresponding to a ratio of amounts of 1 milligram of alpha-chymotrypsin to 20 to 30 milliliters, preferably 25 milliliters of the solution medium, for the treatment and cleaning of the posterior lens capsule left behind in an extracapsular cataract operation.

6 Claims, No Drawings

SOLUTION OF ALPHA-CHYMOTRYPSIN

BACKGROUND OF THE INVENTION

1. Field of the Invention

This invention relates to a compositions of matter useful in performing extracapsular cataract operations and to a method of performing such operations with the use of such compositions. More particularly, the invention relates to the use of a solution of alpha-chymotrypsin in the area of operative treatment of grey cataract.

2. Description of the Prior Art

Grey cataract is an ailment of the eye in which there develops a darkening or clouding of the lens and a decrease of vision produced thereby. By the so called intra-capsular operation, the darkened or clouded lens, which is located in a capsule, is removed by extraction as a whole together with the capsule.

By another method, the so-called extracapsular operation, which is widely used nowadays, the darkened or clouded lens is likewise removed, but the posterior capsule is left behind. Then one proceeds as follows: next, the anterior capsule of the lens is removed. Next, the main part of the lens and the intracapsular posterior rind coating are drawn away with the aid of a flushing process with simultaneous irrigation. There exists also the possibility of using an ultrasonic sound apparatus for the destruction of the main body of the lens and its removal by aspiration. The objective of this operation is to obtain the posterior capsule, in order that a clear division can be maintained between glass body and anterior chamber and to that extent to keep physiological properties or the same. In most cases, there is practiced in such operations the implantation of a posterior chamber lens which replaces the removed darkened or clouded lens. A prerequisite for this is that the posterior capsule is obtained by the operation and that the capsule is completely clear. It is known to mechanically polish the posterior capsule before the implantation of the posterior chamber lens. Despite careful polishing, there frequently develops a so-called capsule fibrosity; this concerns a thickening of the capsule because of very fine particles which cannot be seen microscopically during the operation and form a thickened film on the capsule.

Alpha-chymotrypsin is a substance that in the cleanest, crystallized, dialyzed and stabilized form is obtainable in commerce. The molecular weight is 22,500; the isoelectric point lies between a pH value of 5 to 4; and the effective maximum is at 8.1 to 8.6.

The use of alpha-chymotrypsin is known for the practice of intracapsular operations. There the substance is used in the dilution of 1:5,000 to 1:10,000 and it serves for enzymatic zonulolysis, that is, the dissolution of the zonule fibers that hold the lens in tension. It was therefore surprising to establish, and not foreseeable, that the same substance could be used in a dilution of 1:20,000 to 1:30,000 under conditions that the fibers are not dissolved and the solution can be used for the cleaning of the posterior capsule.

BRIEF SUMMARY OF THE INVENTION

Use of a solution of alpha-chymotrypsin in a physiological solution medium, especially of a physiological saline solution or of a solution of glutathion-bicarbonate according to Edelhauser in a dilution of 1:20,000 to 1:30,000, preferably 1:25,000, corresponding to a ratio of amounts of 1 milligram of alpha-chymotrypsin to 20 to 30 milliliters, preferably 25 milliliters of the solution medium, for the treatment and cleaning of the posterior lens capsule left behind in an extracapsular cataract operation.

DESCRIPTION OF THE PREFERRED EMBODIMENTS

The invention solves the problem of avoiding the above-mentioned thickening of the capsule because of very fine particles which cannot be seen microscopically during the operation and form a thickened film on the capsule, thus obtaining clarity of the posterior capsule.

It has surprisingly been discovered that this can be done with the use of a solution of alpha-chymotrypsin in a physiological solvent medium, especially of a physiological saline solution or a glutathion-bicarbonate solution according to Edelhauser in a dilution of 1:20,000 to 1:30,000, preferably 1:25,000, corresponding to an amount ratio of 1 milligram of alpha-chymotrypsin to 20 to 30 milliliters, preferably 25 milliliters, of the solvent. By treatment of the posterior capsule with such a solution, it is possible to clean it and to remove completely the components of the white of the eye that are gathered on the capsule and can thicken to form a film, and also to hinder or prevent the new formation of such thickening.

Trials, which have been conducted on donor eyes, the corneas of which have been used for complete cornea transplant, have shown that with a solution of alpha-chymotrypsin with the above-mentioned dilution of 1:20,000 to 1:30,000, the fibers that hold the posterior capsule are not dissolved, but rather that exclusively the remaining components on the capsule are removed.

The preparation can be used in the above-indicated dilution for any extracapsular cataract extraction with or without lens implantation, for cleaning of the posterior capsule. A corresponding diluted solution of the preparation can be produced from substances obtainable in commerce, which are furnished in the dry form.

I claim as my invention:

1. A method of performing an extracapsular operation for treatment of grey cataract, said method comprising the step of treating the posterior side of the capsule of the lens by irrigation with a composition of matter consisting essentially of alpha-chymotrypsin in a physiologically suitable solvent medium, said alpha-chymotrypsin being present in a dilution of one part by weight of said alpha-chymotrypsin to between 20,000 and 30,000 parts by weight of said solvent medium.

2. A method as defined in claim 1, wherein said solvent medium is a physiologically suitable solution of sodium chloride.

3. A method as defined in claim 1, wherein said solvent medium is a physiologically suitable solution of glutathion-bicarbonate according to Edelhauser.

4. A method of performing an extracapsular operation for treatment of grey cataract, said method comprising the step of treating the posterior side of the capsule of the lens by irrigation with a composition of matter consisting essentially of alpha-chymotrypsin in a physiologically suitable solvent medium, said alpha-chymotrypsin being present in a dilution effective to clean the posterior lens capsule left behind in said extracapsular cataract operation without dissolving the zonule fibers which hold said lens in tension.

5. A method as defined in claim 4, wherein said solvent medium is a physiologically suitable solution of sodium chloride.

6. A method as defined in claim 4, wherein said solvent medium is a physiologically suitable solution of glutathion-bicarbonate according to Edelhauser.

* * * * *